United States Patent [19]

Kriegler et al.

[11] Patent Number: 5,635,399
[45] Date of Patent: Jun. 3, 1997

[54] RETROVIRAL VECTORS EXPRESSING CYTOKINES

[75] Inventors: Michael Kriegler, Ambler, Pa.; Francis P. McCormick, Albany, Calif.

[73] Assignee: Chiron Corporation, Emeryville, Calif.

[21] Appl. No.: 467,553

[22] Filed: Jun. 6, 1995

Related U.S. Application Data

[63] Continuation of Ser. No. 194,114, Feb. 8, 1994, which is a continuation of Ser. No. 833,801, Feb. 10, 1992, abandoned, which is a continuation of Ser. No. 570,405, Aug. 21, 1990, abandoned, which is a division of Ser. No. 855,865, Apr. 24, 1986, abandoned.

[51] Int. Cl.$^6$ .................. C12N 15/86; C12N 15/19; C12N 15/27; C12N 15/28
[52] U.S. Cl. ............... 435/320.1; 435/172.3; 424/93.2; 424/93.21
[58] Field of Search ................ 435/320.1, 240.1, 435/240.2, 172.3; 424/93.2, 93.21

[56] References Cited

U.S. PATENT DOCUMENTS

| | | | |
|---|---|---|---|
| 4,405,712 | 9/1983 | Vande Woude et al. | 435/5 |
| 4,603,112 | 7/1986 | Paoletti et al. | 435/235.1 |
| 4,650,764 | 3/1987 | Temin et al. | 435/240.2 |
| 4,663,281 | 5/1987 | Gillies et al. | 435/69.1 |
| 4,677,063 | 6/1987 | Mark et al. | 435/69.5 |
| 4,708,818 | 11/1987 | Montanier et al. | 435/5 |
| 4,725,669 | 2/1988 | Essex et al. | 530/322 |
| 4,769,330 | 9/1988 | Paoletti et al. | 435/172.3 |
| 4,868,116 | 9/1989 | Morgan et al. | 435/240.2 |
| 4,879,226 | 11/1989 | Wallace et al. | 435/68.1 |
| 4,980,286 | 12/1990 | Morgan et al. | 435/172.3 |
| 5,091,309 | 2/1992 | Schesinger et al. | 435/69.1 |

FOREIGN PATENT DOCUMENTS

| | | |
|---|---|---|
| 155 198 A1 | 9/1985 | European Pat. Off. . |
| 178 220 A2 | 4/1986 | European Pat. Off. . |
| 2 559 159 | 2/1984 | France . |
| WO85/05619 | 12/1985 | WIPO . |
| WO85/05629 | 12/1985 | WIPO . |
| WO86/00922 | 2/1986 | WIPO . |
| WO86/02380 | 4/1986 | WIPO . |
| WO89/07150 | 8/1989 | WIPO . |

OTHER PUBLICATIONS

Kriegler et al., Cell 38:483–491 (1984).
Joyner et al., Nature 305:556–558 (1983).
Cone et al., Proc. Natl. Acad. Sci. USA 81:6349–6353 (1984).
Eglitis et al., Science 230:1395–1398 (1985).
Anderson, W.F., "Prospects for Human Gene Therapy," *Science*, 226:401–409 (Oct. 26, 1984).
Bender et al., "Evidence that the Packaging Signal of Maloney Murine Leukemia Virus Extends into the gag Region," *J. Virol.*, 61(5):1639–1646 (May, 1987).
Clewall, D.B., "Nature of Col E$_1$ Plasmid Replication in *Escherichia coli* in the Presence of Chloramphenicol," *J. Bacteriol.*, 110(2):667–676 (May, 1972).
Clewell et al., "Supercoiled Circular DNA–Protein Complex in *Escherichia coli*: Purification and Induced Conversion to an Open Circular DNA Form," *Proc. Nat'l Acad. Sci., USA*, 62:1159–1166 (1969).
Coffin, J., Genome Structure, *In: RNA Tumor Viruses*, vol. 2, Weiss et al., (Eds.), 2nd Edition, Cold Spring Harbor Monograph Series, Cold Spring Harbor Laboratory, Cold Spring Harbor, New York, pp. 17–73.
Cohen et al., "Nonchromosomal Antibiotic Resistance in Bacteria: Genetic Transformation of *Escherichia coli* by R–Factor DNA," *Proc. Nat'l Acad. Sci., USA*, 69(8):2110–2114 (Aug., 1972).
Cone et al., "High–efficiency Gene Transfer into Mammalian Cells: Generation of Helper–free Recombinant Retrovirus With Broad Mammalian Host Range," *Proc. Nat'l Acad. Sci., USA*, 81:6349–6353 (Oct., 1984).
Friedmann, "Progress Toward Human Gene Therapy," *Science*, 244:1275–1281 (1989).
Gillio et al., "Retroviral Vector–mediated Gene Transfer and Experssion in Nonhuman Primates Following Autologous Bone Marrow Transplantation," *Annals of the NY Acad. of Sci., Part V*:406–417 (1987).
Hock et al., "Retrovirus–mediated Transfer Expression of Drug Resistance Genes in Human Haematopoietic Progenitor Cells," *Nature*, 320:275–277 (1986).
Joyner et al., "Retrovirus Transfer of a Bacterial Gene into Mouse Haematopietic Progenitor Cells," *Nature*, 305:556–558 (1983).
Kriegler et al., "Transformation Mediated by the SV40 T Antigens: Separation of the Overlapping SV40 Early Genes with a Retroviral Vector," *Cell*, 38:483–491 (Sep., 1984).
Lang et al., "Expression of a Hemopoietic Growth Factor cDNA in a Factor–Dependent Cell Line Results in Autonomous Growth and Tumorigenicity," *Cell*, 43:531–542 (Dec., 1985).
Ledley et al., "Retroviral–medicated Gene Transfer of Human Phenylalanine Hydroxylase into NIH 3T3 and Hepatoma Cells," *Proc. Nat'l Acad. Sci., USA*, 83:409–413 (1986).
Maniatis et al., *Molecular Cloning : A Laboratory Manual*, Cold Spring Harbor Laboratory, Cold Spring Harbor, New York, pp. 252–253 (1982).
Mann et al., "Construction of a Retrovirus Packaging Mutant and Its Use to Produce Helper–Free Defective Retrovirus," *Cell*, 33:153–159 (May, 1983).
Matteucci et al., "Synthesis of Deoxyoligonucleotides on a Polymer Support," *J. Am. Chem. Soc.*, 103:3185–3191 (1981).

(List continued on next page.)

*Primary Examiner*—Mindy Fleisher
*Assistant Examiner*—Johnny F. Railey, II
*Attorney, Agent, or Firm*—Norman J. Kruse; Donald J. Pochopien; Robert P. Blackburn

[57] ABSTRACT

A drug delivery virion which contains an expression system for the desired protein active ingredient packaged in an envelope derived from a retrovirus is especially useful in administering materials which need to cross cell membranes in order to serve their function.

8 Claims, 3 Drawing Sheets

OTHER PUBLICATIONS

Maxam et al., "Sequencing End-Labeled DNA with Base-Specific Chemical Cleavages," *Meth. Enzymol.*, 65:499–561 (1980).

McCormick, D., "Human Gene Therapy: The First Round," *Bio/Technology*, 3:689–693 (1985).

Miller et al., "Improved Retroviral Vectors for Gene Transfer and Expression," *BioTechniques*, 7(9):980–988 (1989).

Sanger et al., "DNA Sequencing with Chain–Terminating Inhibitors," *Proc. Nat'l Acad. Sci., USA*, 74(12):5463–5467 (Dec., 1977).

Southern et al., "Transformation of Mammalian Cells to Antibiotic Resistance with a Bacterial Gene Under Control of the SV40 Early Region Promotor," *J. Mol. Appl. Gen.*, 1:327–341 (1982).

Wang et al., "Molecular Cloning of the Complementary DNA for Human Tumor Necrosis Factor," *Science*, 228:149–154 (Apr. 12, 1985).

Zwiebel et al., "High–Level Recombinant Gene Expression in Rabbit Endothelial Cells Transduced by Retroviral Vectors," *Science*, 243:220–222 (1989).

Bolognesi et al., "Prospects of Treatment of Human Retrovirus–Associated Diseases," *Cancer Research, Supplement*, 45:4700s–4705s (1985).

Carr et al., "Genetic Transformation of Murine Bone Marrow Cells to Methotrexate Resistance," *Blood*, 62(1):180–185 (1983).

Chakrabarti et al., "Expression of the HTLV–III Envelope Gene by a Recombinant Vaccinia Virus," *Nature*, 320:535–537 (1986).

Cline et al., "Gene Transfer in Intact Animals," *Nature*, 284:422–425 (1980).

Cortes et al., "Successful Immunotherapy in a Murine Metastasizing Fibrosarcoma Model," *J. Surg. Onco.*, 25:289–295 (1984).

De Baetselier et al., "Differential Expression of H–2 Gene Products in Tumour Cells is Associated with Their Metastatogenic Properties," *Nature*, 288:179–181 (Nov. 13, 1980).

Donner et al., "McDonough Feline Sarcoma Virus: Characterization of the Molecularly Cloned Provirus and Its Feline Oncogene (v–fms)," *J. Virol*, 41(2):489–500 (1982).

Episkopou et al., "Cell–specified Expression of a Selectable Hybrid Gene," *Proc. Nat'l Acad. Sci., USA*, 81:4657–4661 (1984).

Friedmann, T., "The Future For Gene–Therapy–A Reevaluation," *Ann. N.Y. Acad. Sci.*, 265:141–152 (1975).

Gruber et al., "Retroviral Vector–Mediated Gene Transfer into Human Hematopoietic Progenitor Cells," *Science*, 230:1057–1061 (1985).

Hellerman et al., "Secretion of Human Parathyroid Hormone From Rat Pituitary Cells Infected With a Recombinant Retrovirus Encoding Preproparathyroid Hormone," *Proc. Nat'l Acad. Sci., USA*, 81:5340–5344 (1984).

Holt et al., "Inducible Production of c–fos Antisense RNA Inhibits 3T3 Cell Proliferation," *Proc. Nat'l Acad. Sci., USA*, 83:4794–4798 (1986).

Izant and Weintraub, "Constitutive and Conditional Suppression of Exogenous and Endogenous Genes by Anti––Sense RNA," *Science*, 229:345–352 (1985).

Joyner et al., "Construction and Transfer of Recombinant Retrovirus Clones Carrying the HSV–1 Thymidine Kinase Gene," *The Ontario Cancer Institute, Department of Medical Biophysics, University of Toronto, Toronto, Canada, Development Biology Using Purified Genes*, pp. 535–546 (1981).

Keller et al., "Expression of a Foreign Gene in Myeloid and Lymphoid Cells Derived From Multipotent Haematopoietic Precursors," *Nature*, 318:149–154 (1985).

Lee, R.E., "Gene Therapy: Clipping the Wings of Nature's Own Gene Transfer Vectors," *Can. Med. Assoc. J.*, 134:311–313 (Feb. 15, 1986).

Linial et al., "An Avian Oncovirus Mutant (SE 21Q1b) Deficient in Genomic RNA: Biological and Biochemical Characterization," *Cell*, 15:1371–1381 (1978).

Linial, M., "Transfer of Defective Avian Tumor Virus Genomes by a Rous Sarcoma Virus RNA Packaging Mutant," *J. Virology*, 38(1):380–382 (Apr., 1981).

Mason et al., "The Hypogonadal Mouse: Reproductive Functions Restored by Gene Therapy," *Science*, 234:1372–1378 (1986).

McAleer et al., "Human Hepatitis B Vaccine from Recombinant Yeast," *Nature*, 307:178–180 (1984).

McMichael et al., "Cytotoxic T–Cell Immunity to Influenza," *The New England J. Med.*, 309:13–17 (1983).

Mercola et al., "Insertion of a New Gene of Viral Origin into Bone Marrow Cells of Mice," *Science*, 208:1033–1035 (1980).

Miller et al., "Expression of a Retrovirus Encoding Human HPRT in Mice," *Science*, 225:630–632 (1984).

Miller et al., "Generation of Helper–Free Amphotropic Retroviruses That Transduce a Dominant–Acting, Methotrexate–Resistant Dihydrofolate Reductase Gene," *Mol. And Cell. Biol.*, 5(3):431–437 (1985).

Miller et al., "A Transmissible Retrovirus Expressing Human Hypoxanthine Phosphoribosyltransferase (HPRT): Gene Transfer into Cells Obtained From Humans Deficient in HPRT," *Proc. Nat'l Acad. Sci., USA*, 80:4709–4713 (1983).

Morrow, J.F., "The Prospects for Gene Therapy in Humans," *Ann. N.Y. Acad. Sci.*, 265:13–21 (1975).

Mulligan, R.C., "Construction of Highly Transmissible Mammalian Cloning Vehicles Derived from Murine Retroviruses," *Experimental Manipulation of Gene Expression*, 8:155–173 (1983).

Panicali et al., "Construction of Live Vaccines by Using Genetically Engineered Poxviruses: Biological activity of Recombinant Vaccinia Virus Expressing Influenza Virus Hemagglutinin," *Proc. Nat'l Acad. Sci., USA*, 80:5364–5368 (1983).

Quinnan, Jr. et al., "Cytotoxic T Cells in Cytomegalovirus Infection: HLA–Restricted T–Lymphocyte and Non–T–Lymphocyte Cytotoxic Responses Correlate with Recovery from Cytomegalovirus Infection in Bone–Marrow–Transplant Recipients," *New Eng. J. Med.*, 307:7–13 (1982).

Reif, A.E., "Vaccination of Adult and Newborn Mice of a Resistant Strain (C57BL/6J) against Challenge with Leukemias Induced by Moloney Murine Leukemia Virus," *Cancer Research*, 45:25–31 (1985).

Rein et al., "Myrisylation Site in $Pr65^{gag}$ in Essential for Virus PArticle Formation by Moloney Murine Leukemia Virus," *Proc. Nat'l Acad. Sci., USA*, 83:7246–7250 (Oct., 1986).

Rubenstein et al., "Construction of a Retrovirus Capable of Transducing and Expressing Genes in Multipotential Embryonic Cells," *Proc. Nat'l Acad. Sci., USA*, 81:7137–7140 (1984).

Ruscetti et al., "Three Independent Isolates of Feline Sarcoma Virus Code for Three Distinct gag–x Polyproteins," *J. Virol.*, 35(1):259–264 (1980).

Sabin et al., "History of Sabin Attenuated Poliovirus Oral Live Vaccine Strains," *J. Biol. Standardization*, 1:115–118 (1973).

Shimotohno et al., "Formation of Infectious Progeny Virus after Insertion of Herpes Simplex Thymidine Kinase Gene into DNA of an Avian Retrovirus," *Cell*, 26:67–77 (1981).

Stratowa et al., "Recombinant Retroviral DNA Yielding High Expression of Hepatitis B Surface Antigen," *EMBO J.*, 1(12):1573–1578 (1982).

Stuhlmann et al., "Introduction of a Selectable Gene into Different Animal Tissue by a Retrovirus Recombinant Vector," *Proc. Nat'l Acad. Sci.*, 81:7151–7155 (1984).

Suter et al., "Cytotoxic Immune Response of Puppies to Feline Sarcoma Virus Induced Tumors," *Veterinary Immunology and Immunopathology*, 7:131–138 (1984).

Tabin et al., "Adaptation of a Retrovirus as a Eucaryotic Vector Transmitting the Herpes Simplex Virus Thymidine Kinase Gene," *Mol. Cell. Biol.*, 2(4):426–436 (Apr., 1982).

Townsend et al., "Cytotoxic T Cells Recognize Fragments of the Influenza Nucleoprotein," *Cell*, 42:457–467 (1985).

Wallich et al., "Abrogation of Metastatic Properties of Tumor Cells by *de novo* Expression of H–2K Antigens Following H–2 Gene Transfection," *Nature*, 315:301–305 (1985).

Watanabe et al., "Construction of a Helper Cell Line for Avian Reticuloendotheliosis Virus Cloning Vectors," *Mol. And Cell. Biol.*, 3(12):2241–2249 (1983).

Watanabe et al., "Encapsidation Sequences for Spleen Necrosis Virus, An Avian Retrovirus, are Between the 5' Long Terminal Repeat and the Start of the *gag* Gene," *Proc. Nat'l Acad. Sci., USA*, 79:5986–5990 (1982).

Wei et al., "Construction and Isolation of a Transmissible Retrovirus Containing the *src* Gene of Harvey Murine Sarcoma Virus and the Thymidine Kinase Gene of Herpes Simplex Virus Type 1," *J. Virology*, 39(3):935–944 (1981).

Weis et al., "Eukaryotic Chromosome Transfer: Linkage of the Murine Major Histocompatibility Complex to an Inserted Dominant Selectable Marker," *Proc. Nat'l Acad. Sci., USA*, 81:4879–4883 (1984).

Weis et al., "H–2L$^d$ Antigen Encoded by a Recombinant Retrovirus Genome Is Expressed on the Surface of Infected Cells," *Mol. & Cell. Biol.*, 5(6):1379–1384 (1985).

Yap et al., "Transfer of Specific Cytotoxic T Lymphocytes Protects Mice Inoculated with Influenza Virus," *Nature*, 273:238–239 (1978).

Verma et al., "Expression and Regulation of Rat Growth Hormone Gene in Mouse Fibroblasts," *In: Eukaryotic Viral Vectors*, Gluzman, Y, (Ed.), Cold Spring Harbor Laboratory, pp. 159–164 (1982).

Czarniecki et al., "Synergistic Antiviral and Antiproliferative Activities of *Escherichia coli*–Derived Human Alpha, Beta, and Gamma Interferons," *J. Virology*, 49(2):490–496 (1984).

Temin, H.M., "Retrovirus Vectors For Gene Transfer: Efficient Integration Into and Expression of Exogenous DNA in Vertebrate Cell Genomes," *In: Gene Transfer*, Kucherlapati, R., (Ed.), Plenum Press, New York, pp. 149–187 (1986).

Field et al., "Isolation and Characterization of Acyclovir–resistant Mutants of Herpes Simplex Virus," *J. General Virology*, 49:115–124 (1980).

Irvin, "Purification and Partial Characterization of the Antiviral Protein from *Phytolacca americana* Which Inhibits Eukaryotic Protein Synthesis," *Archives of Biochemistry and Biophysics*, 169:522–528 (1975).

Mulligan et al., "Synthesis of Rabbit β–Globulin in Cultured Monkey Kidney Cells Following Infection with a SV40 β–Globulin Recombinant Genome," *Nature*, 277:108–114 (1979).

Irvin et al., "Purification and Properties of a Second Antiviral Protein from *Phytolacca americana* Which Inactivates Eukaryotic Ribosomes": *Archives of Biochemistry and Biophysics*, 200(2):418–425 (1980).

Stripe et al., "Gelonin, a New Inhibitor of Protein Synthesis, Nontoxic to Intact Cells," *J. Biol. Chem.*, 255(14):6947–6953 (1980).

Parnes et al., "Mouse $\beta_2$–Microglobulin cDNA Clones: A Screening Procedure for cDNA Clones Corresponding to Rare mRNAs," *Proc. Nat'l Acad. Sci., USA*, 78(4):2253–2257 (1981).

Barbieri et al., "Purification and Partial Characterization of Another Form of the Antiviral Protein From the Seeds of *Phytolacca americana* L. (Pokeweed)," *Biochem. J.*, 203:55–59 (1982).

Ball et al., "Monoclonal Antibodies to Myeloid Differentiation Antigens: In Vivo Studies of Three Patients With Acute Myelogenous Leukemia," *Blood*, 62(6):1203–1210 (1983).

Mekalanos et al., "Cholera Toxin Genes: Nucleotide Sequence, Deletion Analysis and Vaccine Development," *Nature*, 306:551–557 (1983).

Dubensky et al., "Direct Transfection of Viral and Plasmid DNA into the Liver or Spleen of Mice," *Proc. Nat'l Acad. Sci., USA*, 81:7529–7533 (1984).

Stanton et al., "Nucleotide Sequence Comparison of Normal and Translocated Murine c–myc Genes" *Nature*, 310:423–425 (1984).

Eglitis et al., "Gene Expression in Mice After High Efficiency Retroviral–Mediated Gene Transfer," *Science*, 230:1395–1398 (1985).

Coussens et al., "Tyrosine Kinase Receptor with Extensive Homology to EGF Receptor Shares Chromosomal Location with *neu* Oncogene," *Science*, 230:1138–1139 (1985).

Lamb et al., "Nucleotide Sequence of Cloned cDNA Coding for Preproricin," *Eur. J. Biochem.*, 148:265–270 (1985).

Tweten et al., "Diptheria Toxin—Effect of Substituting Aspartic Acid for Glutamic Acid 148 on ADP Ribosyltransferase Activity," *J. Biol. Chem.*, 260:10392–10394 (1985).

Rosenberg et al., "Observations on the Systemic Administration of Autologous Lymphokine–Activated Killer Cells and Recombinant Interleukin–2 to Patients with Metastatic Cancer," *New Eng. J. Med.*, 313(23):1485–1492 (1985).

McDougal et al., "Binding of HTLV–III/LAV to T4+T Cells by a Complex of the 110K Viral Protein and the T4 Molecule," *Science*, 231:382–385 (1986).

Pert et al., "Octapeptides Deduced from the Neuropeptide Receptor–like Pattern of Antigen T4 in Brain Patently Inhibit Human Immunodeficiency Virus Receptor Binding and T–Cell Infectivity," *Proc. Nat'l Acad. Sci., USA*, 83:9254–9258 (1986).

Maxwell et al., "Regulated Expression of a Transfected Toxin Gene," *Abstract No. N93, J. Cell. Biochem.*, 0 (10 Part D):39 (Mar. 30, 1986).

RETROVIRAL VECTORS EXPRESSING CYTOKINES

This is a continuation of U.S. application Ser. No. 08/194,114, filed Feb. 8, 1994, which in turn is a continuation of U.S. application Ser. No. 07/833,801, filed Feb. 10, 1992, now abandoned, which in turn is a continuation of 07/570,405, filed Aug. 21, 1990, now abandoned, which in turn is a division of 06/855,865, filed Apr. 24, 1986, now abandoned.

TECHNICAL FIELD

The invention relates to the use of recombinant technology to effect drug delivery. In particular, it concerns the use of commandeered virus envelopes to deliver expression systems for a desired drug such as tumor necrosis factor (TNF).

BACKGROUND ART

So many approaches have been used to effect delivery of drugs to desired target cells that a survey of this field would be both inappropriate and unhelpful. It should be noted, however, that virtually all delivery systems presently employed address the problem of penetrating barriers to the circulatory system of the subject organism and do not address the problem of uptake by particular cells targeted for treatment with the drug. Thus, in the simplest form of ensuring penetration of these barriers, intravenous injection of a solution of an active ingredient, drug delivery merely results in the active ingredient circulating in the blood, but without provision for any special mechanism to ensure that the drug will find its way into the cytoplasm or nucleus of a cell that it is expected either to treat or to kill. While a specific cell may be targeted, e.g., through the use of immunotoxins, either penetration through cellular membranes into the interior cells of interest is effected by whatever mechanisms are made available by the cells themselves, or the appropriate site of the treatment is extracellular.

It is, of course, established that vital particles are capable of introducing foreign nucleic acids and proteins into cells in the normal course of infection. Use of viral particles to transport genetic material into target mammalian cells for purposes of gene therapy appears to be the major approach now being followed to develop this technique. See. e.g., McCormick, D., *Bio/Technology* (1985) 3:689–693. In addition, Lang, R. A., et al. *Cell* (1985) 43:531–542 were able to use a similar system with GM-CSF to induce autocrine growth in a murine blood-cell line. In the Lang work, a cDNA-encoding GM-CSF was inserted into a Moloney murine leukemia-based vector under control of the promoter/enhancer of the vital long-terminal repeat, and infectious, helper-free virus was produced by transfecting into the ψ2-packaging cell line. The GMV virus produced was able to effect GM-CSF production in a hemopoietic cell line. This ability has not heretofore been used to transport designated protein drugs in an intact organism, however.

Retroviruses in particular have been used as vectors for foreign gene insertion, and the general parameters of this use are presently quite well understood: Retroviruses consist of a single stranded RNA genome encapsulated in a protein envelope. The genome itself, reading from the 5' to 3' end, contains a cap, a 5' untranslated region, a segment of RNA designated "ψ" -which is necessary for the RNA to be packaged into protein—i.e., a packaging site, and then the coding sequences for several proteins—the retroviral core protein (gag): reverse transcriptase, to facilitate an intermediate stage consisting of a DNA transcript (pol) and the vital envelope or capsid protein (env), all followed by some 3' untranslated sequences. The three viral proteins are needed for the infectivity of the vital genome: the packaging site is needed to produce additional infective virus.

Retroviruses experience a "proviral" stage which contains a double-stranded cDNA copy of the protein-encoding region of the RNA. However, in this stage, the untranslated 3' and 5' regions are modified to obtain, at either end of this protein-encoding cDNA, a long terminal repeat (LTR) which provides the appropriate promoter and enhancer sequences to effect DNA transcription as well as transcription-terminating sequences at operable positions with respect to the coding portions.

In ordinary infection, the proviral double-stranded cDNA can be integrated into the host cell genome and from there effect the production of additional virus particles containing the RNA genome packaged in its protein capsule. For this procedure to take place, it is critical that the ψ packaging site be present in the provirus.

It has occurred to others that the protein-encoding sequences of the retroviruses could be replaced with those for a desired protein so as to employ the expression systems of the virus when the modified virus infects host cells. See, e.g., U.S. Pat. 4,405,712 and Lang (supra). However, in order to achieve this, the modified vital genome requires a helper virus capable of synthesizing the capsid proteins and packaging the RNA transcripts of the foreign DNA.

Thus, for "gene therapy" the proviral DNA form is inserted into a suitable vector, replicated and packaged into vital envelopes with the aid of a helper virus. For a general review, see Anderson, W. F., *Science* (1984) 226:401–409: Coffin, J., "Genome Structure", in *RNA Tumor Viruses*, Vol 2, Weiss et al, eds, 2d ed, (1985), Cold Spring Harbor, N.Y.

The most commonly used retroviruses for study of gene therapy have been either the murine sarcoma virus (MSV) of the Moloney murine leukemia virus (MoMLV). (Mann, R., et al, *Cell* (1983) 33:153–159.) The proviral form of these retroviruses is isolated and inserted into more or less standard bacterial cloning vectors for amplification. The proviral insert, which contains the gag-, pol- and env-encoding mRNA flanked by long terminal repeats containing the control sequences, along with a packaging site is then manipulated to replace the region containing the protein-encoding RNA with the desired foreign gene. If this DNA is transfected into host cells which have been infected with complete virus or with defective virus lacking only the packaging site, the RNA which is synthesized from the modified provirus is then packaged into virions for reinfection of another cell. This provides a mechanism for introduction of the DNA encoding the desired active ingredient or drug into the cell by infection.

There are two ways to go about this. In one approach, the modified proviral DNA is transfected into cells which bear an infection from the unmodified virus, co-residing in the cell. The normal vital vectors will synthesize the packaging materials and some of the mRNA produced by the modified provirus will be packaged in a manner analogous to the normal virion and then can be used to infect target cell for the production of protein. Along with these commandeered vital envelopes, however, will be a certain number of repackaged normal viruses which, if not separated from the "delivery truck" viruses simply cause additional virus infection in host cells infected with the products of this virion production round.

In a more useful approach, the provirus cloning vector containing the desired gene is used to transfect a cell which has been genetically modified to produce defective vital envelopes which contain no viral genomic RNA—in effect, empty delivery trucks. These cells are obtained by integration of the proviral form of a mutant retrovirus lacking the ψ packaging site, and several such cell lines are available in the art to all that request them. Two of these lines, designated ψ-1 or ψ-2 are extensively described in Mann, R., et al, *Cell* (1983) 33:153–159 (supra) and are made by transfecting host NIH-3T3 fibroblast cells with a plasmid containing MoMLV proviral inserts from which the ψ packaging site had been deleted. The ψ-2 cells apparently produce several empty viral envelopes per cell corresponding to the vital envelope of the native virus in the course of a generation. When these cells are transfected with proviral DNA containing both a foreign gene and the packaging site, ψ, they package the mRNA transcript from the proviral DNA containing the foreign gene into these empty envelopes to generate modified viruses which can infect any cells (murine in this case) which are normally hosts for MoMLV. It should be noted, however, that this recombinant, modified virus is defective in that it cannot cause the production of additional modified (or other) virions in the cell it "infects". It is able to cause the production of the protein the gene encodes in the "infected" cell, but the infection cannot spread to additional cells because no additional virions are produced.

More useful than ψ2 for preparation of medicaments for humans in the present invention are the ψ-AM lines, which are available from Cone, R. D., et al, *Proc Natl Acad Sci (USA)* (1984) 81:6349–6353. These lines are also obtained by transfecting NIH-3T3 cells, but with a vector designated pMAV-ψ$^-$. This vector also contains an insert of a defective provirus which lacks the ψ packaging site. However, pMAV-ψ$^-$ is a hybrid encoding the gag-pol sequences of MoMLV and envelope sequences derived from the amphotropic virus 4070A. The empty capsids produced by these cell lines package RNA transcripts of cotransfected modified proviral DNA to produce pseudo viruses which recognize and infect human, rat, and mouse cells.

Thus, the art provides a system for moving genes into susceptible cells which has been, in the past, employed only for gene therapy or for generation of autocrine growth factors. These methods inevitably utilize an ex-vivo exposure of targeted cells to the retroviral vector; for example, in gene therapy, bone marrow cells are removed and treated, and then reimplanted. In the present invention, an analogous system is mustered to deliver pharmaceuticals to target cells using conventional methods of administration to produce a highly dead-end, localized "infection".

DISCLOSURE OF THE INVENTION

The invention is directed to highly unusual pharmaceutical compositions and to methods for delivering active drugs to cells of organisms susceptible to vital infection. The target organisms are ordinarily vertebrates. In one embodiment, the pharmaceutical composition is composed of delivery viruses which contain envelope proteins capable of causing transient and non-replicative infection of the cells in the subject organism to be treated with the drug. These pharmaceutical compositions are administered by injection into the blood stream or by localized injection into masses of undesirable cells such as tumor cells.

Thus, in one aspect, the invention relates to a drug delivery system which comprises a delivery retrovirus. The retrovirus has a "genome" comprising an RNA which encodes the desired active protein ingredient operably linked to control sequences which were derived from a retrovirus and to a ψ packaging site, and an envelope protein which is capable of effecting the infection of a target host cell with the virion, so that the target host cell alone is "infected", but unable to pass this infection to additional cells.

In another aspect, the invention relates to a method of administering an active protein ingredient to a subject vertebrate host which comprises administering this drug delivery system either locally or systemically.

In still other aspects, the invention relates to materials and processes significant in the preparation of the above-described drug delivery system. These include a proviral DNA comprising a DNA sequence encoding a desired active protein ingredient operably linked to control sequences derived from a retrovirus, including a packaging site, and flanked by retroviral-derived LTRs as well as ψ$^{31}$ cells transfected with this proviral DNA.

In another embodiment, the general method of the invention can also be carried out by implanting ψ$^-$ cells transfected with the proviral DNA of the previous paragraph, or cells infected with the pseudo virions they produce to effect in situ production of the desired protein. Accordingly the cotransfected ψ$^-$ cells and cells infected with the modified viruses they produce provide pharmaceutical compositions which are also aspects of the invention.

Also an aspect of the invention is a process to prepare the compositions thereof which comprises isolating the delivery virions produced by the foregoing ψ$^-$ packaging cells.

MODES OF CARRYING OUT THE INVENTION

A. Definitions

Figure 1:
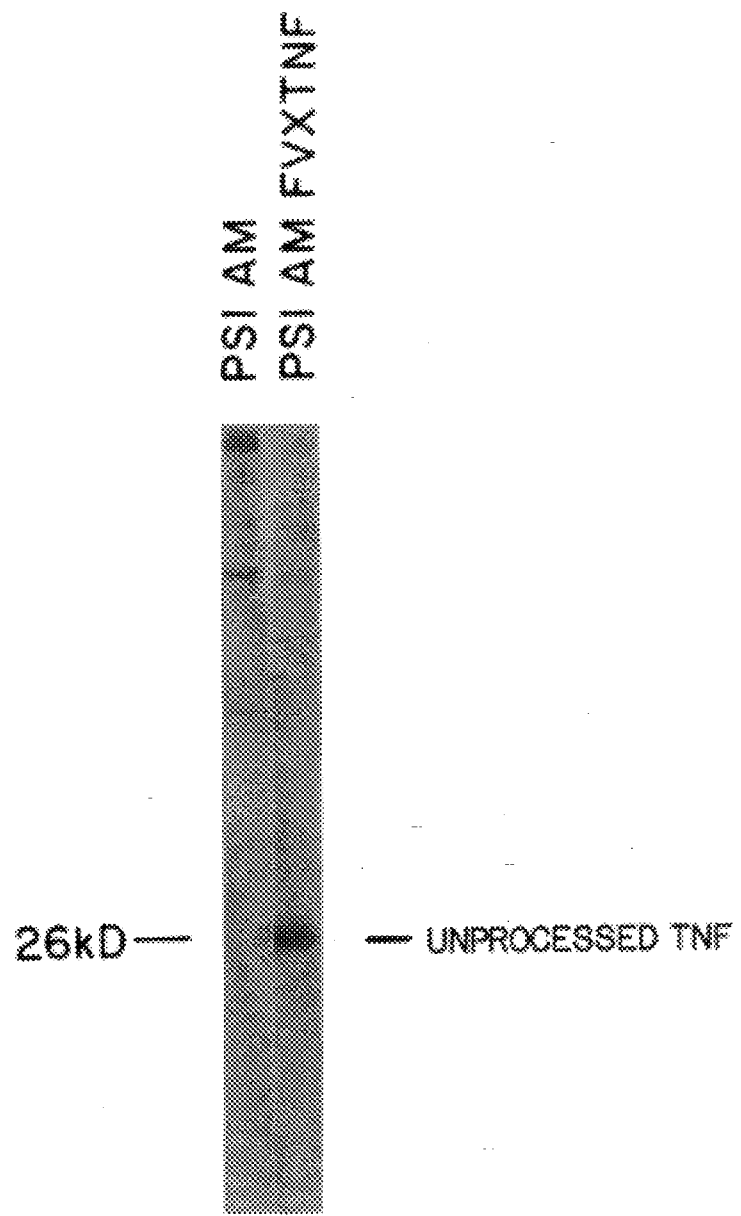
FIG. 1 shows a radioautograph of $^{35}$S-methionine labeled TNF in lysates of ψ-AM (packaging) cells transfected with pFVX-TNF.

As used herein, "drug delivery virion" refers to a modified retrovirus wherein the genome is an RNA which contains control sequences derived from retroviral nucleic acids operably linked to the coding sequences for an "active ingredient" protein. The genome is packaged in a protein envelope which is compatible with, and capable of causing "infection" with the contained genome in, a subject intended to be treated with the protein. The infection in this case extends only to the entry of the desired RNA into the cell and production of the protein; no additional infective virions are produced.

Thus, "dead-end" infection describes a modified form of infection wherein the vital envelope facilitates the entry of the modified virus into the cytoplasm, and the contained genome is expressed, but no new virions are produced.

"Control sequences" refers to those nucleic acid sequences containing, for example, promoters and, often, enhancers which are necessary and sufficient for the production of the desired active protein ingredient by expression of the coding sequence operably linked to it.

In the case of the drug delivery retrovirions of the invention, the RNA genome and its proviral counterpart also includes the ψ packaging site.

"Nucleic acid sequences" will sometimes be employed herein as a generic term covering both DNA and RNA fragments. As the materials of the invention include retroviral genomes and their proviral counterparts, particular functional sequences referred to will occur both in RNA and DNA form. The corresponding loci will be referred to interchangeably for their occurrences in both DNA and RNA, as it will be understood that in the ordinary course of infection, such functionalities are, indeed, interchangeable. For example, the ψ packaging site apparently is operable in the RNA genome to be packaged: however, the corresponding sequences occur in the proviral DNA. Similarly, promoter, enhancer, and terminator sequences occur, though in slightly different forms, in both the genomic RNA and proviral DNA forms. The interchangeability of these functionalities in the various phases of the viral life cycle is understood by those in the art, and accordingly, rather loose terminology in regard to DNA or RNA status is often used in referring to them. Specifically, sequences specified by a progression of bases should be understood to include these specific sequences and their complements, both in DNA and RNA forms.

The pharmaceutical compositions of the invention include the drug delivery virions produced by transfected intermediate cells which have been transformed with ψ⁻ helper provirus and thus produce empty envelopes. For simplicity in referring to these cells used in the preparation of this composition, these cells will be referred to as "packaging" cells.

The resulting delivery virions can also be used to infect wild type cells in vitro, for example, as models for their ability to cause production of the desired protein in the target host. These infected cells are referred to herein as "tester" cells.

B. General Description

The crucial intermediate in the preparation of the compositions of the invention is a proviral DNA vector containing the coding sequence for the protein drug to be administered. The DNA encoding such active protein ingredient may be obtained from any convenient source and, depending on the protein chosen, can be synthesized chemically, recovered from a cDNA library, isolated from genomic DNA, or otherwise obtained by means known in the art.

The proteins to be administered according to the method of the invention include any protein which has a desired effect on an infected cell in the subject to be treated. Advantages of the drug delivery system of the invention are experienced especially when the protein operates within the cytoplasm of a target cell. For example, tumor necrosis factor (TNF) is capable of selectively killing tumor cells, but needs to transit the cell membrane to exert its effect. Other proteins, such as ribotoxins and the various colony-stimulating factors, also operate intracellularly.

The system of the invention is applicable also to materials whose function is carried out outside the target cells or which function by binding to receptors on the cell surface. In this case, however, the drug delivery virions are administered indirectly as an implant of transfected packaging cells or of tester cells which have been infected with the drug delivery virions. For example, tissue plasminogen activator or urokinase, which act in the bloodstream itself, directly on soluble enzymes in the blood, could be produced in situ by these implanted cells.

DNAs encoding the foregoing proteins are available in the art, and can be obtained bracketed with linker sequences for convenient manipulation, if desired. The nature of the delivery system is such that both genomic and cDNA sequences can be used, since introns can be processed in the environment transfected by the provirus. The protein drug can be encoded in the delivery virion to specify any form of the protein desired—for example, an active form, a mature form, a fused protein, a preprotein, or a preproprotein. In the example below, a cDNA clone encoding TNF is used as the source of the coding sequence; however, clearly this is illustrative only, and any other desired coding sequence could also be employed.

The proviral transfer vector is obtained by isolation of an appropriate proviral form of a retrovirus such as the commonly used murine sarcoma virus (MSV), Moloney murine leukemia virus (MoMLV). Harvey sarcoma virus (HaSV), or a variety of other retroviruses. Since the proteins associated with the virion per se are deleted in the construction, even infectious retroviruses which cause disease in humans, such as hepatitis, HTLVI, and LAVI, could also be used, although it is not necessary to utilize such materials which, of course, have the potential for psychological resistance among the subjects to be treated.

The proviral form of the selected retrovirus is obtained by propagating the virus in tissue culture, isolating proviral DNA, cloning this proviral DNA into a γ phage cloning vector, and propagating the recombinant vector in a susceptible bacterial hose where the phage vector is integrated. The proviral DNA is excised and reisolated. The provirion is then provided with suitable linkers and inserted into a bacterial cloning vector for amplification. Suitable bacterial cloning vectors include pBR322, pML, or vectors of the pUC series. These may need to be modified to eliminate or alter restriction sites and so forth, as is understood by those skilled in the art. The cloning vectors are restricted and then provided with inserts of the linker-framed provirions.

The native provirion inserts contain the vital protein encoding sequences flanked by long terminal repeat (LTR) sequences and contain the packaging site adjacent one of the LTRs. These protein-encoding sequences between the packaging site and the other LTR are then eliminated by appropriate restriction and/or exonuclease digestion and replaced by linker or poly-linker sequences. The appropriate sites may be already available in the intervening region, or if not, these can be obtained using site-directed mutagenesis, as is understood in the art.

After amplification, the vectors containing the modified provirions are cleaved with suitable restriction enzymes to open the vectors for insertion of the desired coding sequence. Since the control sequences, except for the packaging site, are in the long terminal repeats, insertion of a desired protein-encoding drug sequence into the linker places it in operable linkage with the controls. The resulting modified virion then becomes an expression system for the desired protein instead of for the vital proteins, and still retains a packaging site to permit this modified vital genome to be infective.

These drug delivery provirion DNAs are amplified and isolated using known techniques to provide a source of transfecting DNA for the ψ⁻ packaging cells.

If desired, the inserted coding sequence in the modified virion can also include a marker sequence. However, a significant decrease in expression of the inserted sequence is observed when the marker sequence is placed 3' of the insert. This can be avoided, as transfection of the ψ⁻ packaging cells can be coincident with transformation with vectors containing a suitable marker, most appropriately the G418 resistance marker. Any suitable marker can, of course, be used, and such markers include, for example, Ecogpt conferring resistance to mycophenolic acid and DHFR sequences conferring methotrexate resistance.

The modified provirion, along with a marker plasmid, if necessary, is transfected into recipient packaging cells using standard transfection techniques such as calcium phosphate precipitation. The transformants are grown in culture appropriate to their particular cell type; the ψ⁻ 3T3 cells illustrated below are cultured under conditions generally used for wild-type 3T3 cells. Of course, an appropriate amount of a selective component of the medium, such as G418, is also included to select successful transformants.

The transformed packaging cells can be shown successfully to produce the proteins encoded by the inserted coding sequences in the modified virion by assessing the concentration of protein in the medium or cell lysate, as appropriate.

To obtain the packaged recombinant virions, the supernatant from the packaging cells is separated from the cells, for example, by using a 0.45 µ filter. The virus is obtained from the filtrate by, for example, high-speed centrifugation to harvest the vital particles or the filtrate is used per se. The concentrated vital particles or the filtrate are then formulated as pharmaceutical compositions.

In addition, the virion preparation can be assessed for competence to effect drug delivery to target cells by using a tester cell line, for example, the wild-type counterpart of the packaging cell line, which produces no empty vital capsules, or any cell line susceptible to infection by the virus and, preferably, also, to the protein produced by the recombinant virion. The amount of desired protein produced by this tester cell can be assessed, and, in the case of the appropriate cells, this assessment can be by the direct effect of the protein on the cells.

Both the packaging and tester cells can also be used as implants to provide a source of the protein drug in situ.

C. Utility and Administration

The drug delivery system of the invention is effective in the net result of transiting protein materials into cells where they may exert their effects. The transfer occurs by virtue of vital infection so it is merely necessary to juxtapose the drug delivery virions with the target cells. If the target cells are localized in, for example, a solid tumor the composition of the invention may be infected directly into the solid tumor. If the cells are, however, widely distributed such as in a leukemia or where, for example, red blood cells or bone marrow cells are needed to be targeted, systemic intravenous infection is required.

The virions are prepared for infection in typical ways suitable for administration of drugs by suspension in isotonic saline or other suitable pharmaceutical excipient as is known in the art.

Implantation of packaging or tester cells is conducted by formulating them into suitable compatible formulations, such as physiological saline, and directly injecting them into the desired location. The cells can also be formulated using encapsulation techniques. (See, e.g., U.S. Pat. No. 4,391,909.)

D. Standard Methods

Depending on the host cell used, transformation is done using standard techniques appropriate to such cells. The calcium treatment employing calcium chloride, as described by Cohen, S. N., *Proc Natl Acad Sci (USA)* (1972) 69:2110, or the RbCl$_2$ method described in Maniatis et al, *Molecular Cloning: A Laboratory Manual* (1982) Cold Spring Harbor Press, p. 254 was used for procaryotes or other cells which contain substantial cell wall barriers. For mammalian cells without such cell walls, the calcium phosphate precipitation method of Graham and van der Eb, *Virology* (1978) 52:546 is preferred.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution: in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol and resuspension in 10 mM Tris, 1 mM EDTA, pH 7.5. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 5–10 µM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared by the triester method of Matteucci et al (*J Am Chem Soc* (1981) 103:3185) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM MgCl$_2$, 5 mM dithiothreitol, 1–2 mM ATP, 1.7 pmoles γ32P-ATP (2.9 mCi/mmole), 0.1 mM spermidine, 0.1 mM EDTA.

Ligations are performed in 15–30 µl volumes under the following standard conditions and temperatures: 20 mM Tris-Cl pH 7.5, 10 mM MgCl$_2$, 10 mM DTT, 33 µg/ml BSA, 10 mM-50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per µg of vector at 60° C. for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form: 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered. Details of site specific mutation procedures are described below in specific examples.

Correct ligations for plasmid construction are confirmed by first transforming *E. coli* strain MM294 obtained from *E. coli* Genetic Stock Center, CGSC #06135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci* (USA) (1969) 62:1159, optionally following chloramphenicol amplification (Clewell, D. B., *J Bacteriol* (1972) 110:667). The isolated DNA is analyzed by restriction and/or sequenced by the dideoxy method of Sanger. F., et al, *Proc Natl Acad Sci* (USA) (1977) 74:5463 as further described by Messing et al. *Nucleic Acids Res* (1981) 9:309, or by the method of Maxam et al, *Methods in Enzymology* (1980) 65:499.

Host strains used in cloning and expression herein are as follows:

For cloning and sequencing, *E. coli* strain HB101 was used as the host.

For M13 phage recombinants, *E. coli* strains susceptible to phage infection, such as *E. coli* K12 strain DG98 are employed. The DG98 strain has been deposited with ATCC 13 Jul. 1984 and has accession number 1965.

E. Examples

The following examples are intended to illustrate but not to limit the invention.

EXAMPLE 1

Preparation of Modified Provirion Containing TNF

The coding sequences for human TNF were obtained from the clone pE4, a cDNA clone extensively described in U.S. Ser. No. 760,661, filed 30 Jul. 1984, assigned to the same assignee and incorporated herein by reference. This clone is also on deposit at ATCC, ATCC# 39894, deposited 15 Oct. 1984.

The plasmid pAW711, also there described, and deposited 8 Nov. 1984, ATCC# 39918 can also be used as a source of TNF sequences.

The vector containing the retroviral control system in proviral form along with the packaging site is a derivative of pEVX: pEVX contains the LTRs and ψ site from MoMLV inserted into the EcoRI site of pML (Kreigler, M. J., et al, *Cell* (1984) 38:483–491). pEVX was modified to eliminate a splice donor site by replacing a SmaI/BalI segment with a 978 bp SamI/SmaI fragment from the Harvey sarcoma virus (HaSV), which contains the 3' portion of the 5' LTR and the 5' portion of the HaSV genome. The resulting construct was digested completely with SstII and partially with BglII to obtain a 669 bp fragment lacking nonessential HaSV regions. This fragment was gel purified and religated to SmaI/BalI digested pEVX. The resulting vector pFVXM, which was deposited with the American Type Culture Collection, Rockville, Md. on Apr. 23, 1986 in accordance with the Budapest Treaty, having ACTT Accession No. 67103 contains a polylinker between the LTR fragments derived from MoMLV and includes the packaging site from this virus, but lacks the splice donor site in the upstream LTR.

The pFVXM vector is amplified in *E. coli* strain HB101, and the plasmid DNA isolated. pE4 is likewise amplified in *E. coli* HB101 and reisolated as plasmid DNA. Both preparations of plasmid DNA are treated with PstI (to excise the TNF-encoding region from pE4 and to open pFXVM in the polylinker region). Ligation of the fragments is carried out using standard conditions and the ligation mixture transformed into *E. coli* HB101 to $Amp^R$. Plasmid DNA was again isolated, and correct orientation of the insert was established by restriction analysis. Recombinant plasmids with the correct orientation of the TNF-encoding sequences are designated pFVX-TNF, and used to transfect appropriate packaging cells as described below.

In a similar manner, for example, pFVXM may be digested with PstI and ligated to DNA sequences encoding ricin A toxin, CSF-1, and urokinase, each provided with suitable PstI linkers when needed. The resulting vectors are designated pFVX-RA. pFVX-CSF, and pFVX-UK. respectively.

EXAMPLE 2

Production of Drug Delivery Retrovirions

The pFVX-TNF prepared in Example 1 (10 µg) is mixed with 1 µg of pRSV-NEO (Southern et al. *J Mol Appl Gen* (1982) 1:327–341), which contains the marker sequences conferring resistance to the antibiotic G418. The DNA mixture was added at 1 µg/ml to DMEM medium containing 10% fetal calf serum and the solution was brought to 30 µg/ml of polybrene. The resulting solution was poured onto $8\times10^5$ ψ-AM cells (Mann et al, supra) in a 60 mm Petri plate and the plate was incubated at 37° C. in a $CO_2$ incubator for 6 hr. After an initial growth period, the cells were grown on selection medium containing 400 µg/ml G418 and resistant colonies were picked, and transferred to 24-well tissue culture dishes for testing for TNF production.

The cellular proteins were labeled with either $^{35}S$-cysteine or $^{35}S$-methionine. The cells were first cultured on DMEM lacking cysteine or methionine, but containing 5% dialyzed fetal calf serum, for 30 min at 37° C. to effect cysteine or methionine starvation. One hundred µCi of $^{35}$S-cysteine or $^{35}$S-methionine having a specific activity of approximately 400 Ci/mmol was added and the cells further incubated for 2 hr at 37° C. The supernatant was removed and saved. The cells were lysed with lysis buffer and the lysate supernatant was also recovered by centrifugation. Both the clarified lysate and culture supernatant were tested for the presence of TNF as follows:

Polyclonal antisera to TNF prepared in rabbits were added to each test material in a centrifuge tube and incubated at 4° C. for 1 hr with shaking. This was followed by the addition of a 50% suspension (v/v) of protein A attached to Sepharose CL4B and followed by incubation at 4° C. for 30 min.

The beads were pelleted in a microfuge and washed. The precipitated material was removed from the beads by boiling in SDS. The solubilized TNF-containing solutions were loaded onto 12.5% polyacrylamide gel for electrophoresis and the proteins were fixed and stained as well as read by autoradiography. The results are shown in FIGS. 1 and 2.

FIG. 1 shows the results of labeling with $^{35}$S-methionine Label appears only in the leader sequence of the 26 kd unprocessed protein in the lysate: no label is present in the mature, 17 kd, secreted form (which does not contain methionine residues).

Figure 2:
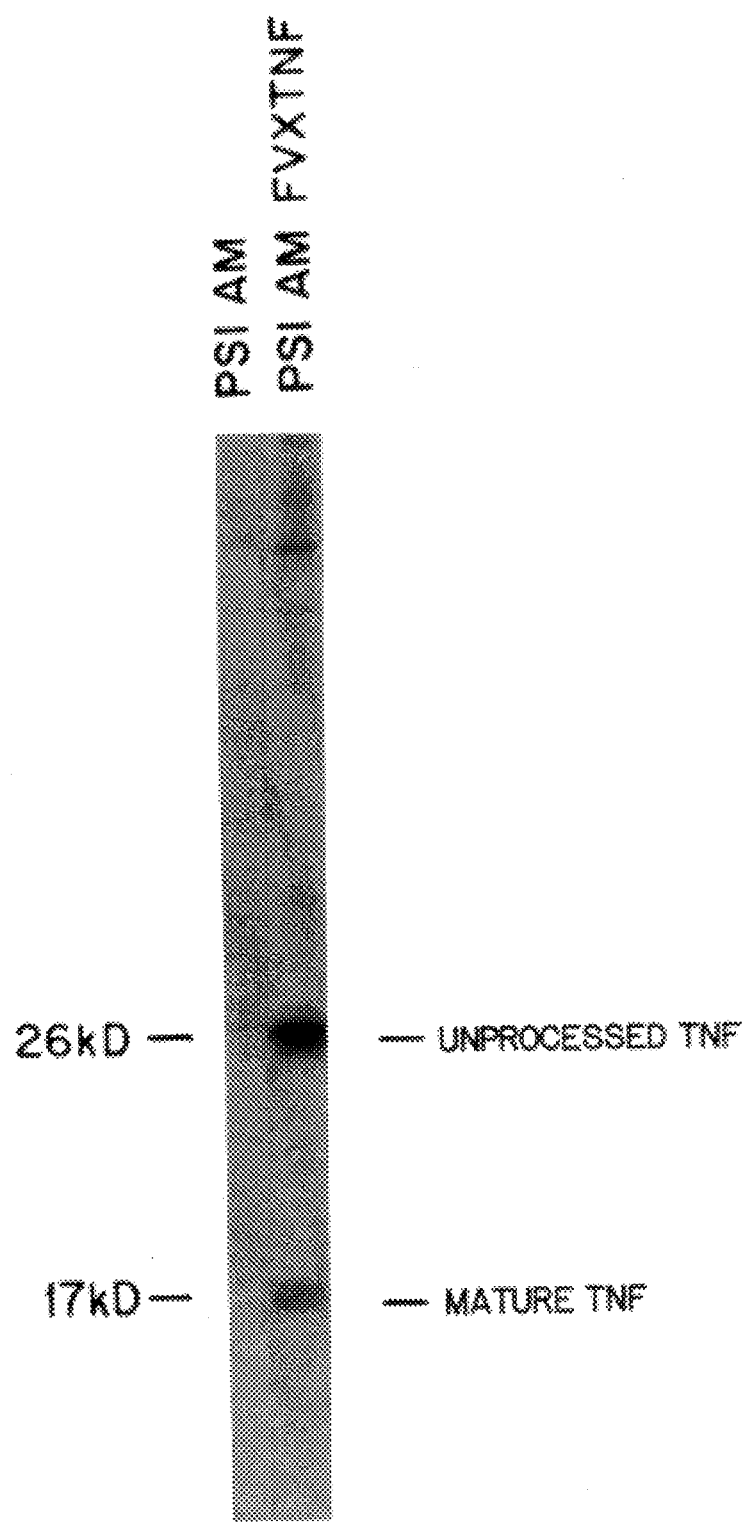
FIG. 2 shows a radioautograph of $^{35}$S-cysteine labeled TNF in lysates of ψ-AM (packaging) cells transfected with pFVX-TNF.

FIG. 2 shows the results of $^{35}$S-cysteine labeling: both the unprocessed and mature forms are labeled, as expected.

Cell supernatants were also assayed for TNF using the L-929 assay below. The ability of these supernatants to show TNF activity was completely destroyed by preincubation with the rabbit anti-TNF antisera.

EXAMPLE 3

Recovery of Drug Delivery Virions

The supernatants from the cells of Example 2 which secreted TNF into the medium were filtered through 0.45 microns Millipore filter to ensure that no cells were transferred. The filtered supernatant contains the recombinant virion designated TNF-V.

EXAMPLE 4

Dead-End Infection of Tester Cells

Figure 3:
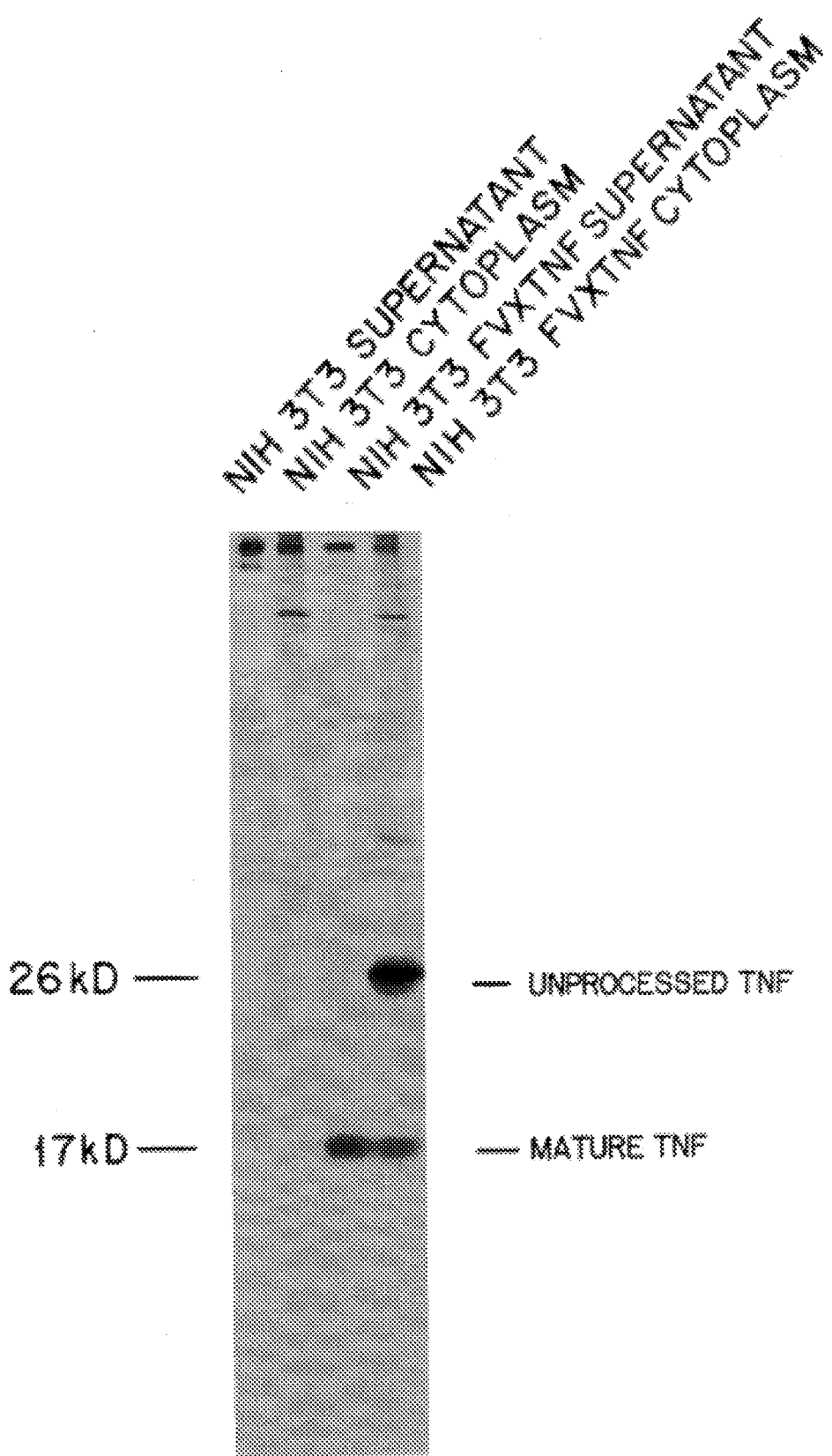
FIG. 3 shows a radioautograph of $^{35}$S-cysteine labeled TNF in supernatants and lysates of tester cells infected with TNF delivery virions.

The TNF-V prepared in Example 2 was used to infect $1 \times 10^5$ NIH 3T3 or RAT2 cells by incubation at 37° C. overnight in a $CO_2$ incubator. Cell supernatants and lysates were analyzed for TNF production using $^{35}$S-cysteine labeling, immunoprecipitation and radioautography exactly as described above in Example 2. The results for infected cells are shown in FIG. 3. Both the 17 kd and 26 kd forms of TNF contain label.

Supernatant from these cells also showed TNF activity using the L-929 cytotoxicity assay, which activity was removed by incubation with rabbit anti-TNF antisera.

Assay for TNF Activity

To assay biological activity of the TNF, the L-929 assay system was also used. The L-929 cells are prepared overnight as monolayers in microtiter plates. The test samples are diluted 2-fold across the plate. UV irradiated, ahd then added onto the prepared cell monolayers. The culture media in the wells are then brought to 1 µg/ml actinomycin D. The plates are allowed to incubate 18 hr at 37° C. and the plates are scored visually under the microscope. Each well is given a 25, 50, 75 or 100% mark signifying the extent of cell death in the well. One unit of TNF activity is defined as the reciprocal of the dilution at which 50% killing occurs.

In addition, a more sensitive version of this assay was developed that monitors the release of $^{35}$S labeled peptides from prelabeled cells, when treated with the test sample and actinomycin D. This version of the assay can be used to quantitate potency, e.g., to evaluate the relative potency of oocyte translated material. Briefly, actively growing L-929 cultures are labeled with $^{35}$S methionine (200 µCi/ml) for 3 hr in methionine-free media supplemented with 2% dialyzed fetal calf serum. The cells are then washed and plated into 96 well plates, incubated overnight, and treated the next day with 2-fold dilutions of test samples and 1 µg/ml actinomycin D. The cultures were then incubated at 37° C. for 18 hr. 100 µl supernatant aliquots from each well were then transferred onto another 96 well plate, acid (TCA) precipitated, and harvested onto glass fiber filters. The filters were washed with 95% ethanol, dried and counted. An $NP_{40}$ detergent control is included in every assay to measure maximum release of radioactivity from the cells. The percent $^{35}$S release is then calculated by the ratio of the difference in count between the treated cells and untreated controls divided by the difference between $NP_{40}$ treated cells and untreated controls, i.e., by the ratio:

$$\% \text{ release} = \frac{\text{sample} - \text{cell control}}{NP_{40} - \text{cell control}} \times 100.$$

Higher TNF potency results in higher values of this ratio.

The following plasmids have been deposited at the American Type Culture Collection, Rockville. Md. USA (ATCC) under the terms of the Budapest Treaty on the International Recognition of the Deposit of Microorganisms for the Purposes of Patent Procedure and Regulations thereunder (Budapest Treaty) and are thus maintained and made available according to the terms of the Budapest Treaty. Availability of such stains is not to be construed as a license to practice the invention in contravention of the rights granted under the authority of any government in accordance with its patent laws.

The deposited plasmids have been assigned the indicated ATCC deposit numbers. The plasmids have also been deposited with the Master Culture Collection (CMCC) of Cetus Corporation, Emeryville, Calif., USA, the assignee of the present application, and assigned the indicated CMCC deposit numbers:

| Plasmid or Cell Line | CMCC Deposit No. | ATCC Deposit No. | Date of ATCC Deposit |
|---|---|---|---|
| pE4 |  | 39894 | 15 October 1984 |
| pAW |  | 39918 | 8 November 1984 |
| pFVXM |  | 67103 | 23 April 1986 |

The foregoing written specification is considered to be sufficient to enable one skilled in the art to practice the invention. The deposit of materials herein does not constitute an admission that the written description herein contained is inadequate to enable the practice of any aspect of the invention, including the best mode thereof, nor is this deposit to be construed as limiting the scope of the claims to the specific illustrations which materials deposited represent.

We claim:

1. A replication defective retroviral particle capable of infecting a human cell, said retroviral particle having an RNA sequence therein encoding a human protein, said RNA sequence operably linked to a promoter and expressible in said human cell, said protein being a cytokine or tissue plasminogen activator.

2. The retroviral particle of claim 1, wherein said protein is capable of acting intracellularly.

3. The retroviral particle of claim 2, wherein said cytokine is a colony stimulating factor.

4. The retroviral particle of claim 3, wherein said colony stimulating factor is CSF-1.

5. The retroviral particle of claim 1, wherein said protein is secretable and capable of acting extracellularly.

6. The retroviral particle of claim 5, wherein said protein is the cytokine TNF or tissue plasminogen activator.

7. The retroviral particle of claim 6, wherein said protein is TNF.

8. The retroviral particle of claim 1 having an envelope protein selected from the group consisting of MoMLV, MSV, HaSV, HTLVI and LAVI.

* * * * *